United States Patent [19]
McCue et al.

[11] Patent Number: 5,996,404
[45] Date of Patent: Dec. 7, 1999

[54] ON-LINE DENSE PASTE RHEOLOGICAL TESTING APPARATUS AND METHOD

[75] Inventors: John Craig McCue, Covington; Richard Eric Nordgren, Daleville, both of Va.

[73] Assignee: Westvaco Corporation, New York, N.Y.

[21] Appl. No.: 09/138,382

[22] Filed: Aug. 24, 1998

[51] Int. Cl.[6] .................................................. G01N 11/00
[52] U.S. Cl. ........................................ 73/54.01; 73/54.43
[58] Field of Search .............................. 73/54.01, 54.04, 73/54.11, 54.43, 54.14, 54.13

[56] References Cited

U.S. PATENT DOCUMENTS

| | | |
|---|---|---|
| 2,550,802 | 5/1951 | Gholson . |
| 3,933,032 | 1/1976 | Tschoegl . |
| 4,238,952 | 12/1980 | Koopmann et al. . |
| 4,607,532 | 8/1986 | Arthur et al. . |
| 5,172,585 | 12/1992 | Gleissle . |
| 5,269,190 | 12/1993 | Kramer et al. . |
| 5,307,680 | 5/1994 | Drescher-Krasicka . |
| 5,417,106 | 5/1995 | Grudzien, Jr. et al. . |
| 5,699,273 | 12/1997 | Hinzpeter et al. . |

*Primary Examiner*—Hezron Williams
*Assistant Examiner*—Jay L. Politzer
*Attorney, Agent, or Firm*—J. R. McDaniel; R. L. Schmalz

[57] ABSTRACT

This invention relates to an on-line instrument that is able to sample the contents of a dense paste-like material, isolate the material, measure the material's rheological properties by extruding it under pressure and perform a self-cleaning operation. Such structures of this type, generally, provide precise measurements of the material's rheological properties (deformation and flow under pressure) such as yield stress, yield pressure, viscosity or Bingham number.

17 Claims, 3 Drawing Sheets

10

ON-LINE DENSE PASTE RHEOLOGICAL TESTING APPARATUS AND METHOD

BACKGROUND OF THE INVENTION

1. Field of the Invention

This invention relates to an on-line instrument that is able to sample the contents of a dense paste-like material, isolate the material, measure the material's rheological properties by extruding it under pressure and perform a self-cleaning operation. Such structures of this type, generally, provide precise measurements of the material's rheological properties (deformation and flow under pressure) such as yield stress, yield pressure, viscosity or Bingham number.

2. Description of the Related Art

It is known to employ devices for measuring properties of powdered or granular materials. Exemplary of such prior art is U.S. Pat. No. 4,607,532 ('532) to J. R. F. Arthur et al., entitled "Apparatus for Determining the Behavior of Powdered Material Under Stress". While the '532 device is capable of measuring the properties of powdered or granular materials, these materials are vastly different from dense paste-like materials, such as carbon.

It is also known to employ various rheological apparatus which are capable of measuring various materials. Exemplary of such prior art are U.S. Pat. No. 4,238,952 ('952) to R. Koopmann et al., entitled "Method of Determining Characteristic Rheological Quantities of Visco-Elastic Materials" and U.S. Pat. No. 5,269,190 ('190) to O. Kramer et al., entitled "Apparatus for the Performance of Rheological Measurements on Materials". While the '952 reference teaches a device that is capable of measuring certain rheological properties of visco-elastic materials, such as rubber compounds, this device is not capable of providing information regarding the onset of flow as a function of pressure, i.e., yield pressure. Also, while the '190 reference employs the use of rheological measurements, these are measurements of material creep and stress relaxation by the loading of a test specimen in an axial manner and not yield pressure.

Finally, it is known to employ capillary rheometers. Exemplary of such prior art are U.S. Pat. No. 5,172,585 ('585) to W. Gleissle, entitled "Continuously Operating Capillary Rheometer Apparatus with Minimized Response-Time Lag" and U.S. Pat. No. 5,417,106 ('106) to C. P. Grudzien, Jr., et al., entitled "Capillary Rheometer Plunger Pressure Transducer and Measurement Technique". While these references teach various capillary rheometer apparatus, they are concerned with measuring properties of polymer melts which are vastly different materials from a dense paste-like material, such as carbon.

It is apparent from the above that there exists a need in the art for an apparatus which can measure the rheological properties of dense paste-like materials and which is capable of providing information regarding onset of flow as a function of pressure.

It is a purpose of this invention to fulfill this and other needs in the art in a manner more apparent to the skilled artisan once given the following disclosure.

SUMMARY OF THE INVENTION

Generally speaking, this invention fulfills these needs by providing a dense paste rheological testing apparatus, comprising of a dense paste introduction means; a dense paste collection means located substantially adjacent to the dense paste introduction means; a dense paste pressurization means located substantially adjacent to the dense paste collection means; a dense paste property sampling means located substantially adjacent to the dense paste collection means; and an apparatus controller means operatively connected to the dense paste introduction means, the dense paste collection means, the dense paste pressurization means and the dense paste property sampling means.

In certain preferred embodiments, the dense paste collection means includes a slide gate. Also, the dense paste collection means consists of a piston and die. Also, the dense paste pressurization means consists of the piston. Finally, the dense paste property sampling means consists of an orifice and an onset of extrusion sensor.

In another further preferred embodiment, the present invention allows for the precise measurement of a material's rheological properties (deformation and flow under pressure) such as yield stress, yield pressure, viscosity or Bingham number.

The preferred testing apparatus, according to this invention, offers the following advantages: rheological testing of dense paste; ease of assembly and repairs; good stability; good durability; and excellent economy. In fact, in many of the preferred embodiments, these factors of rheological testing of dense paste and economy are optimized to the extent that is considerably higher than heretofore achieved in prior, known rheological testing apparatus.

The above and other features of the present invention, which will become more apparent as the description proceeds, are best understood by considering the following detailed description in conjunction with the accompanying drawings, wherein like characters represent like parts throughout the several views and in which:

DETAILED DESCRIPTION OF THE INVENTION

Figure 1:
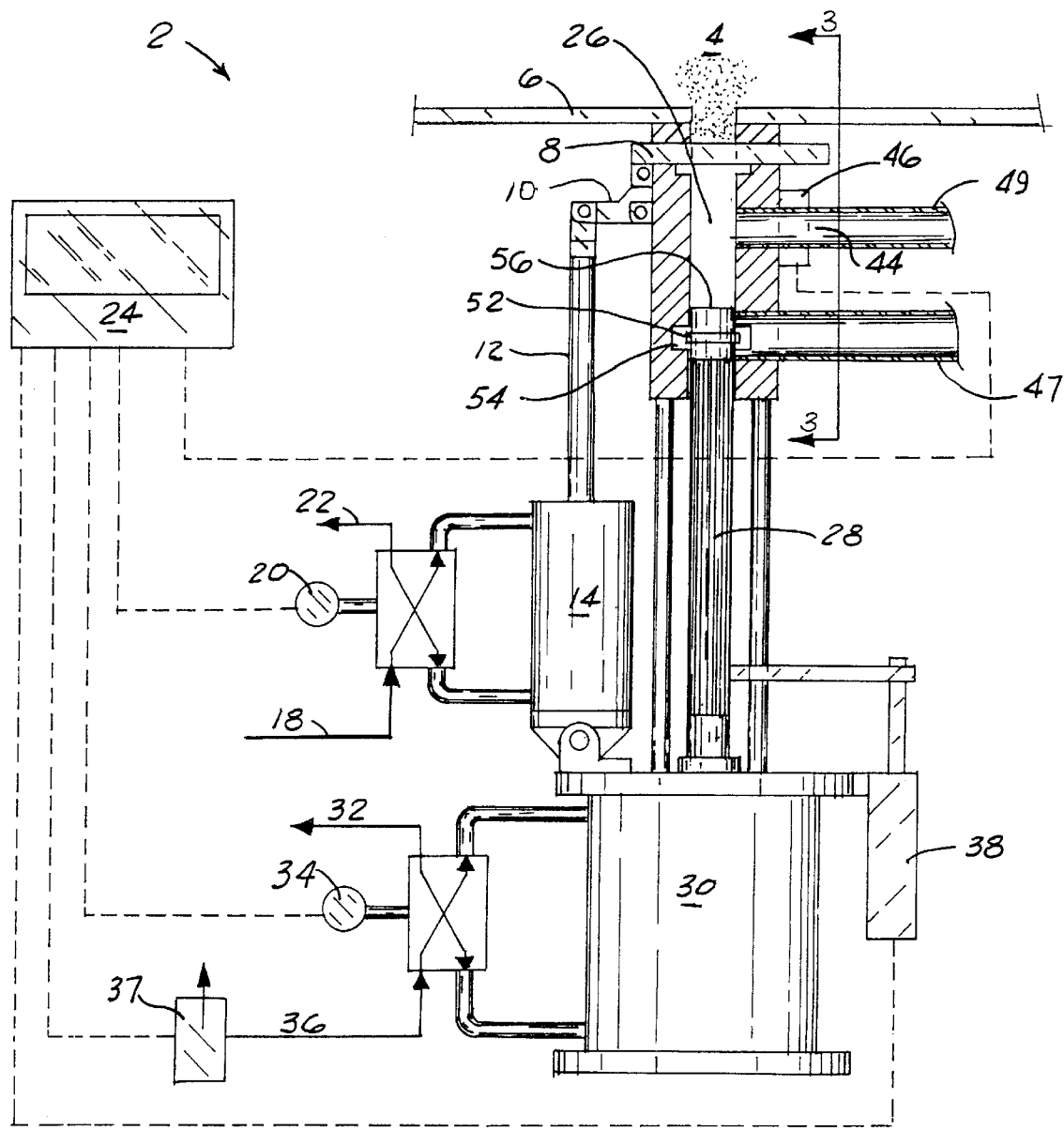
FIG. 1 is a schematic illustration of a dense paste rheological testing apparatus, according to the present invention.

With reference first to FIG. 1, there is illustrated an advantageous environment for the use of the concepts of this invention. In particular, the dense paste rheological tester 2 is shown. Tester 2 includes, in part, dense paste 4, dense paste mixing vat floor 6, slide gate 8, slide gate arm 10, conventional pneumatic piston 12, conventional pneumatic cylinder 14, conventional pressure source 18, conventional four-way valve 20, conventional vent 22, controller 24, cylindrical die 26, conventionally fluted extrusion piston 28, conventional pneumatic cylinder 30, conventional vent 32, conventional four-way valve 34, conventional pressure source 36, conventional pneumatic servo-valve 37, conventional linear-variable differential transformer (LVDT) 38, orifice 44, conventional sensor 46 and ports 47 and 49.

It is to be understood that dense paste 4, preferably, is carbon. Controller 24, preferably, is any suitable digital computer controller that is capable of operating the various pneumatic cylinders and pistons and retrieving data from onset of extrusion sensor 46. Sensor 46, preferably, is any suitable photo sensor, such as an infrared photo sensor. However, for electrically conductive paste like carbon, sensor 46 may be a conventional electrical continuity tester. Finally, port 47 is conventionally attached to any suitable pressurized fluid source (not shown), such as steam, water or air.

The starting configuration of tester 2 is with slide gate 8 open and piston 28 fully extended such that the sample port in vat floor 6 is closed off and piston 28 is flush with the top surface of the bottom of the mixing vat floor 6. In its fully extended state, any remaining previously tested material, which has not been removed by the self-cleaning operation, will be removed and only freshly produced dense paste 4 will be tested. A sample 4 is drawn by retracting piston 28 and allowing the cavity of die 26 to fill with sample 4 by action of an agitator in the vat (not shown). Once die 26 has been filled, slide gate 8 shuts and pneumatic cylinder 30 is pressurized by conventional techniques. Servo-valve 37 conventionally regulates the pressure inside of pneumatic cylinder 30. Pressurization continues to the point of extrusion of sample 4 through orifice 44, which is sensed by photo sensor 46. Pressure in cylinder 30 is recorded by controller 24 at the onset of extrusion. The pressure in cylinder 30 is slowly relieved to the point that piston 28 stops moving, as sensed by the LVDT 38. The pressure in cylinder 30 is again recorded at this point by controller 24. The two recorded pressures can be used to conventionally calculate the sample rheological properties, such as yield pressure.

Figure 2:
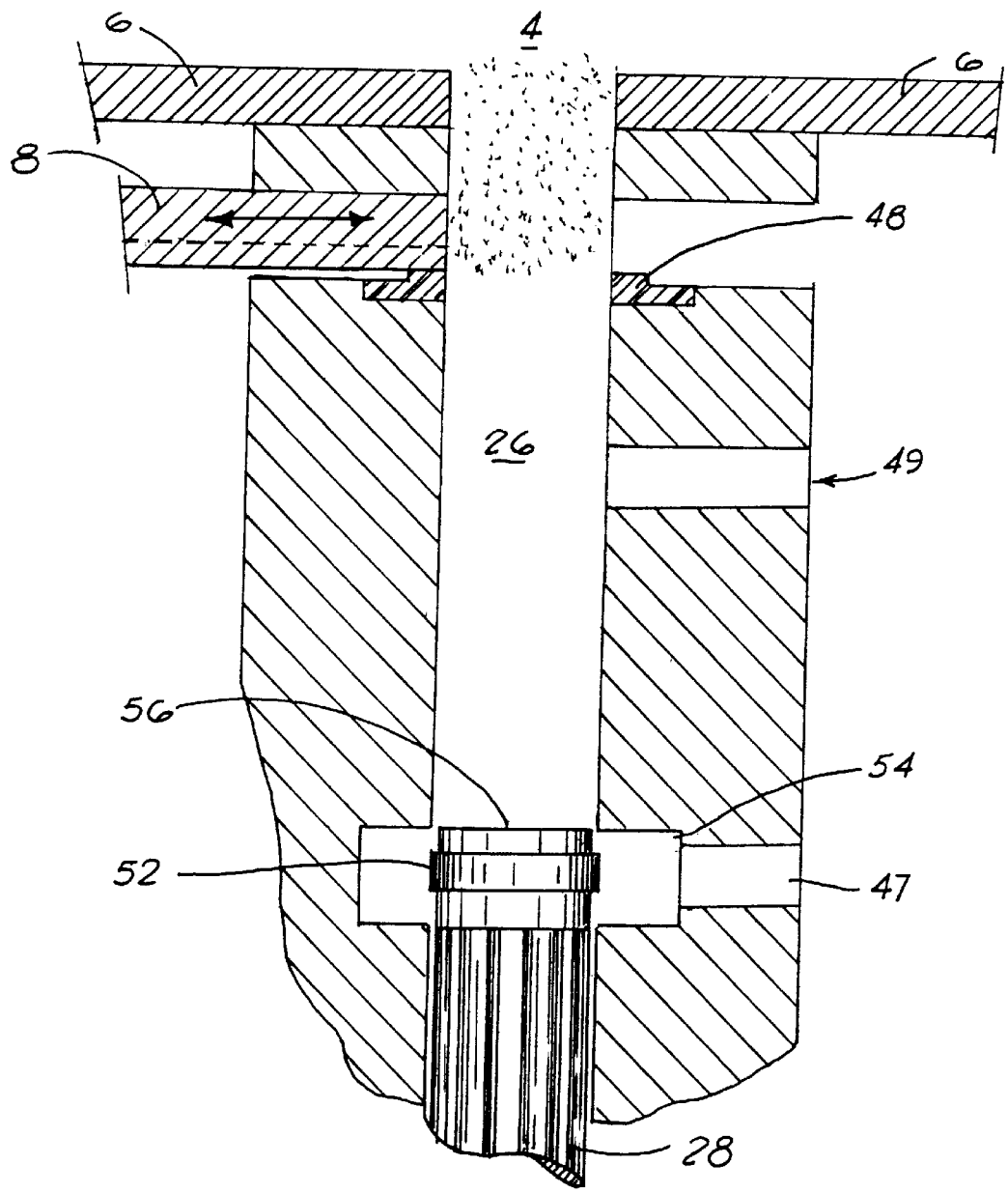
FIG. 2 is a schematic illustration of a cutaway side view of the seal and extrusion die of the dense paste rheological tester, according to the present invention.
Figure 3:
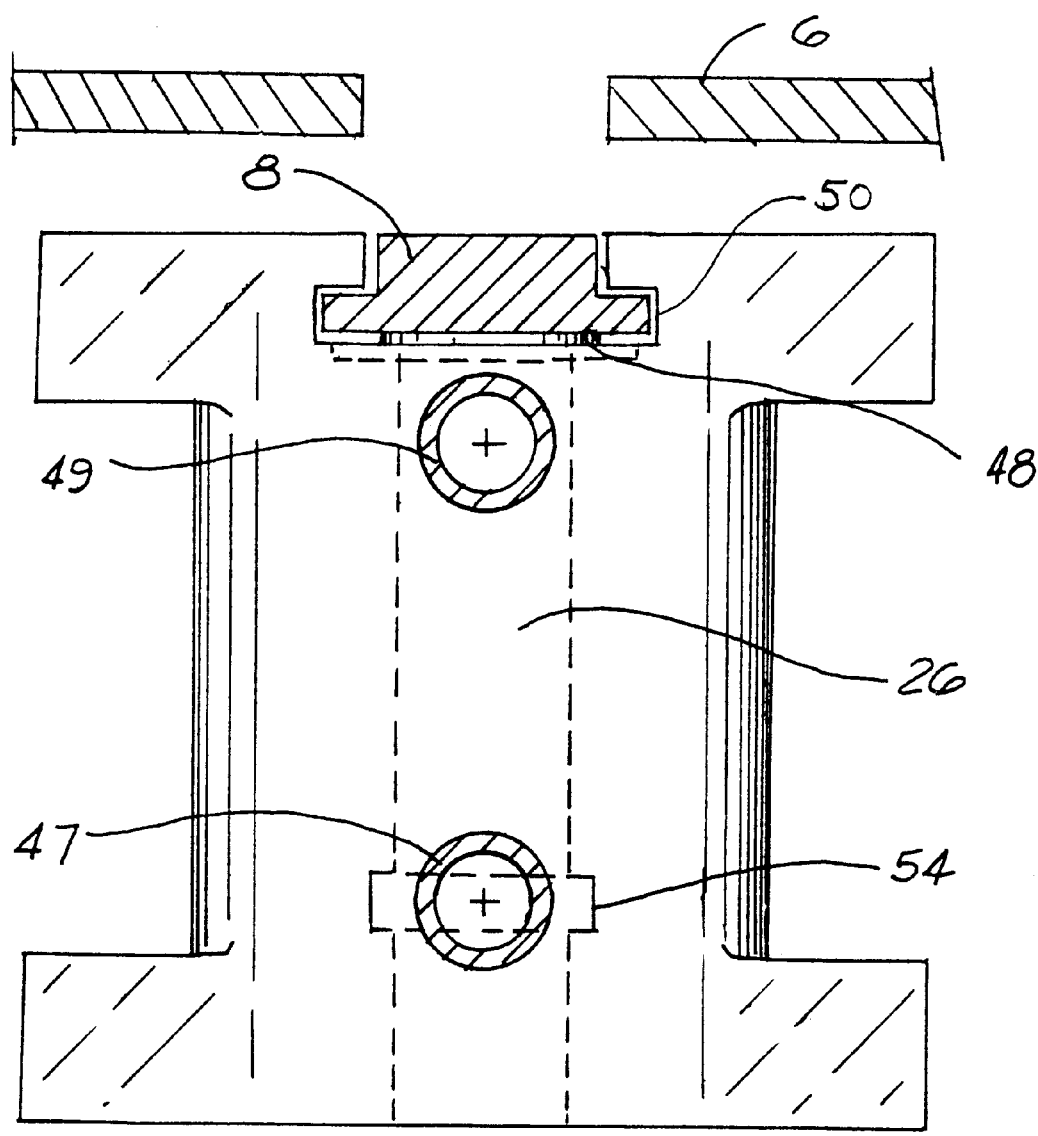
FIG. 3 is a side view taken along lines 3—3 of FIG. 1, which illustrates the upper seal and its housing, according to the present invention.

In order to retain the solvent or surfactant properties of sample 4 within die 26 once it has been pressurized, a special seal 48 (FIG. 2) located between slide gate 8 and die body 26 is to be utilized. As shown in FIG. 3, seal element 48 is an annular ring and is, preferably, made from Teflon®. As shown in FIG. 3 seal 48 rests in a circular recess 50 that is cut into the body of die 26 and is compressed between slide gate 8 and die body 26 by a small amount, preferably, 0.003 in.

A second seal 52, (FIG. 2) also annular in shape and constructed from Teflon®, rests in a recess 54 cut into the extrusion piston 28. The seal 54 is slightly compressed between the extrusion piston 28 and the internal wall of the die body 26 and held in place by metallic cap 56.

Another important aspect of the present invention is its self-cleaning aspect. This is accomplished by using a liquid, such as water and compressed air. Piston 28 is retracted below the level of port 47 (FIG. 2). After die 26 has been isolated by shutting slide gate 8, water is fed through port 47 into die 26 thereby filling the cavity. Cylinder 30 is then pressurized, thereby expelling the carbon plug from the extrusion orifice 44 through outlet port 49. After piston 28 is retracted, high pressure air is fed through port 47, drying the internal surfaces of dies 26 and completing the cleaning cycle. Also, water and air can be fed through port 47 as piston 28 is pressurized towards gate 8. In this manner, the water and air can clean the fluted surface of piston 28.

Once given the above disclosure, many other features, modifications or improvements will become apparent to the skilled artisan. Such features, modifications or improvements are, therefore, considered to be a part of this invention, the scope of which is to be determined by the following claims.

What is claimed is:

1. A dense paste rheological testing apparatus, wherein said paste is comprised of:
   a dense paste introduction means;
   a dense paste collection means located substantially adjacent to said dense paste introduction means;
   a dense paste pressurization means located substantially adjacent to said dense paste collection means;
   a dense paste property sampling means located substantially adjacent to said dense paste collection means; and
   an apparatus controller means operatively connected to said dense paste introduction means, said dense paste collection means, said dense paste pressurization means and said dense paste property sampling means, wherein said apparatus is further comprised of a cleaning means for said dense paste collection means and said dense paste property sampling means located adjacent to said dense paste property sampling means, wherein said cleaning means is further comprised of a port means and a pressurized fluid means operatively connected to said port means.

2. The apparatus, as in claim 1, wherein said dense paste introduction means is further comprised of:
   an opening means.

3. The apparatus, as in claim 2, wherein said opening means is further comprised of:
   a slide gate.

4. The apparatus, as in claim 1, wherein said dense paste collection means is further comprised of:
   a cylindrical hole means.

5. The apparatus, as in claim 4, wherein said cylindrical hole means is further comprised of:
   a die.

6. The apparatus, as in claim 1, wherein said dense paste pressurization means is further comprised of:
   a fluted piston; and
   a piston elongation measurement means.

7. The apparatus, as in claim 6, wherein said piston elongation measurement means is further comprised of:
   a linear-variable differential transformer.

8. The apparatus, as in claim 1, wherein said dense paste property sampling means is further comprised of:
   a dense paste sample collection means; and
   a dense paste sample measuring means.

9. The apparatus, as in claim 8, wherein said dense paste sample collection means is further comprised of:
   an orifice.

10. The apparatus, as in claim 8, wherein said dense paste sample measuring means is further comprised of:
    a sensor means located substantially within said dense paste sample collection means.

11. The apparatus, as in claim 1, wherein said apparatus controller means is further comprised of:
    a dense paste introduction means controller means:
    a dense paste collection means controller means;
    a dense paste pressurization means controller means;
    a dense paste property sampling means controller means; and
    a data collection means operatively connected to said dense paste introduction means controller means, said dense paste collection means controller means, said dense paste pressurization means controller means and said dense paste property sampling means controller means.

12. The apparatus, as in claim 11, wherein said data collection means is further comprised of:
    a computer means.

13. A method for testing rheological properties of a dense paste, including a dense paste introduction means, a dense paste collection means, a dense paste pressurization means, a dense paste property sampling means, wherein said method is comprised of the steps of:

operating said dense paste introduction means;

collecting a dense paste in said dense paste collection means;

pressurizing said dense paste in said dense paste collection means by said dense paste pressurization means such that said pressurized dense paste is introduced into said dense paste property sampling means;

collecting a portion of said pressurized dense paste in said dense paste property sampling means; and measuring rheological properties of said pressurized dense paste in said dense paste property sampling means, wherein said method is further comprised of the step of cleaning said dense paste collection means and said dense paste property sampling means by passing a pressurized fluid through a port means located substantially adjacent to said dense paste property sampling means.

14. The method, as in claim 13, wherein said step of operating said dense paste introduction means is further comprised of the step of:

operating a slide gate.

15. The method, as in claim 13, wherein said step of collecting said dense paste is further comprised of the step of:

collecting said dense paste in a cylindrical hole means.

16. The method, as in claim 13, wherein said dense paste pressurization step of further comprised of the step of:

contacting said dense paste with a piston.

17. The method, as in claim 13, wherein said step of collecting a portion of said pressurized dense paste is further comprised of the step of:

introducing said portion of said pressurized dense paste into an orifice.

* * * * *